United States Patent [19]

Houbion et al.

[11] 4,182,622

[45] Jan. 8, 1980

[54] 3-PHENACYLIDENE PHTHALIDE SAFENING AGENTS

[75] Inventors: John A. Houbion, Kirkwood; David E. Schafer, Creve Coeur, both of Mo.

[73] Assignee: Monsanto Company, St. Louis, Mo.

[21] Appl. No.: 929,133

[22] Filed: Jul. 28, 1978

[51] Int. Cl.$^2$ .......................... A01N 9/00; A01N 9/20
[52] U.S. Cl. .......................................... 71/88; 71/118; 260/343.3 R
[58] Field of Search ................................... 71/88, 118

[56] References Cited

U.S. PATENT DOCUMENTS

| | | | |
|---|---|---|---|
| 3,547,620 | 12/1970 | Olin | 71/118 |
| 3,564,768 | 2/1971 | Hoffmann | 71/100 |
| 3,663,200 | 5/1972 | Olin | 71/118 |
| 3,702,759 | 11/1972 | Hoffmann | 71/77 |
| 3,719,466 | 3/1973 | Ahle | 71/88 |
| 3,985,773 | 10/1976 | Alt et al. | 71/88 |
| 3,989,503 | 11/1976 | Pallos et al. | 71/100 |
| 4,021,224 | 5/1977 | Pallos et al. | 71/100 |
| 4,033,756 | 7/1977 | Hoffmann | 71/100 |

OTHER PUBLICATIONS

Katekar, "Inhibitors of the Geotropic etc.," (1976), Phytochem. 15, pp. 1421–1424 (1976).
Brown et al. I, "The Effect on Root Geotropism etc.," (1973), Pest. Sci. 4, pp. 473–484 (1973).
Brown et al. II, "New Inhibitors of Amin Transport," (1972), Experientia 28, pp. 1290–1291 (1972).

*Primary Examiner*—Glennon H. Hollrah
*Attorney, Agent, or Firm*—Arnold H. Cole; Donald W. Peterson

[57] ABSTRACT

Certain 3-phenacylidene phthalides have been found useful as safening agents to reduce herbicidal injury to rice plants.

27 Claims, No Drawings

3-PHENACYLIDENE PHTHALIDE SAFENING AGENTS

This invention relates to compositions containing a herbicide and a safening agent therefor, and to methods of using such compositions to reduce herbicidal injury to treated crop plants. More particularly, this invention is concerned with novel compositions which comprise butachlor herbicide and a 3-phenacylidene phthalide. The invention is also concerned with the methods of treating upland rice plants, or the plant growth medium, with such novel compositions to prevent or reduce the injury to said rice plants which would otherwise occur due to use of the herbicide alone.

BACKGROUND OF THE INVENTION

Butachlor is the recognized common name for the active herbicide ingredient 2-chloro-2′,6′-diethyl-N-(butoxymethyl)acetanilide. The preparation of this compound and the manner in which it is employed to control the growth of undesired plants are described in U.S. Pat. Nos. 3,442,945 and 3,547,620. In addition, the use of butachlor as a selective herbicide to control the growth of undesired grasses in the presence of rice is described in U.S. Pat. No. 3,663,200. While this latter patent indicates only minimal herbicidal injury to the treated rice plants, it will be noted that the rates of treatment are relatively low.

In the case of upland rice, it is often desirable to use higher rates of the active herbicide ingredient to achieve more rapid or more complete control of the undesired grasses which compete with the crop. Such higher rates, however, can create a significant problem because of the increased level of the detrimental herbicidal effect on the rice crop.

DESCRIPTION OF THE INVENTION

The effect of 3-phenacylidene phthalide and a number of derivatives thereof on root geotropism in various plants is discussed in the literature. Tests of the parent compound on cress and ryegrass are described in Experientia, Vol. 28, pgs. 1290–1 (1972), and on cress alone in Phytochemistry, Vol. 15, pgs. 1421–4 (1976). The same two plants were tested with said parent compound and a few derivatives as described in Pesticide Science, Vol. 4, pgs. 473–84 (1973).

In accordance with the present invention, it has been found that herbicidal injury to the upland rice plants can be prevented or reduced in magnitude by employing butachlor herbicide in conjunction with certain 3-phenacylidene phthalides which serve as safening agents.

The 3-phenacylidene phthalides which are employed in the practice of this invention have the formula

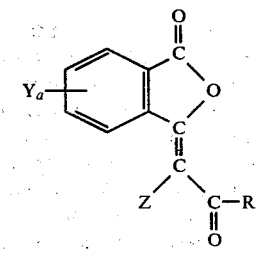

wherein R is selected from phenyl,

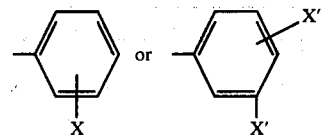

X is selected from methyl, trifluoromethyl, bromo, fluoro, 2′-chloro, 2′-nitro, 4′-phenyl and 2′ or 3′-methoxy, X′ is methoxy or ethoxy, Y is selected from 4-methoxy and 4 or 5-chloro, Z is hydrogen or bromo, and a is zero or one. It will be recognized that the compounds of this formula contain a carbon-to-carbon double bond with two different groups or atoms attached to each carbon. Such compounds may thus exist in the form of cis and trans geometric isomers, and both of said isomers, along with mixtures thereof, are contemplated within the scope of this invention.

These compounds can be prepared by methods known in the prior art, or they can be prepared by the method described in copending application Ser. No. 898,272, filed Apr. 20, 1978. This latter method involves the dehydrohalogenation of an α-halo or α,α-dihalo-3-phenacylphthalide. The reaction is carried out in an inert organic solvent and in the presence of a tertiary amine base which serves as a hydrogen halide acceptor.

Representative examples of the compounds within the scope of the above formula include:

| | | |
|---|---|---|
| 1. | 4′-bromo-3-phenacylidene phthalide, | m.p. 220° C. |
| 2. | 2′-methoxy-3-phenacylidene phthalide, | m.p. 114° C. |
| 3. | 2′-chloro-3-phenacylidene phthalide, | m.p. 98° C. |
| 4. | 3-phenacylidene phthalide, | m.p. 105° C. (cis), 162° C. (trans) |
| 5. | 3′-methyl-3-phenacylidene phthalide, | m.p. 113°–115° C. |
| 6. | 3′-methoxy-3-phenacylidene phthalide, | m.p. 118°–119° C. |
| 7. | 2′,5′-dimethoxy-3-phenacylidene phthalide, | m.p. 136° C. |
| 8. | 3′-trifluoromethyl-3-phenacylidene phthalide, | m.p. 148°–149° C. |
| 9. | 2′-nitro-3-phenacylidene phthalide, | m.p. 180.5° C. |
| 10. | 3′,5′-dimethoxy-3-phenacylidene phthalide, | m.p. 174°–175° C. |
| 11. | 4′-phenyl-3-phenacylidene phthalide, | m.p. 164°–165° C. |
| 12. | 4′-fluoro-3-phenacylidene phthalide, | m.p. 140°–141° C. |
| 13. | 3′,4′-dimethoxy-3-phenacylidene phthalide, | m.p. 166° C. |
| 14. | α-bromo-3-phenacylidene phthalide, | m.p. 138°–139° C. |
| 15. | 5-chloro-3-phenacylidene phthalide, | m.p. 162°–164° C. |
| 16. | 4-methoxy-3-phenacylidene phthalide, | m.p. 165° C. |
| 17. | 4-chloro-3-phenacylidene phthalide, | m.p. 148° C. |
| 18. | 2′,4,5′-trimethoxy-3-phenacylidene phthalide, | m.p. 156° C. |
| 19. | 2′,5′-diethoxy-3-phenacylidene | |

| | |
|---|---|
| -continued | |
| phthalide, | m.p. 122°-123° C. |

The safening agents of this invention may be applied in a mixture with butachlor herbicide, or the components of the mixture can be used sequentially. In the case of a sequential treatment, the safening agent may be applied either before or after application of the herbicide. Effective herbicidal amounts of butachlor are well understood by those skilled in the art, and such amounts are used together with an effective safening amount of a 3-phenacylidene phthalide. The ratio of herbicide to safening agent may vary depending upon the age of the plants at time of treatment, climatic conditions, soil, etc. It is generally preferred, however, to employ a weight ratio of herbicide to safening agent ranging from 1:5 to 5:1.

Application of the herbicide and safening agent, in admixture or in sequence, may be made directly to the plants or to parts thereof such as stems, leaves, etc. Alternatively, the application can be made to the plant growth medium.

The effectiveness of the 3-phenacylidene phthalides for the purposes of this invention is demonstrated by test results reported below. The representative compounds employed serve only to illustrate the novel aspects of the invention and should not be construed as a limitation on its scope. Said results are obtained in accordance with the following test procedures.

A good grade of top soil is placed in a container and compacted to a depth of approximately 1.27 cm. from the top of said container. A predetermined number of rice seeds are placed on top of the compacted soil. A quantity of soil sufficient to substantially fill the container is measured and placed in a second container. A measured quantity of the safening agent dispersed or dissolved in a suitable carrier is applied to the soil in the second container. A measured quantity of the butachlor herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and butachlor herbicide, and the container is leveled. The container is then placed on a sand bench in the greenhouse and watered from below as needed. The plants are observed at the end of approximately 21 days and the results in terms of percent inhibition of each seed lot are recorded. At the start of each test, a container is also prepared containing no butachlor herbicide and no safening agent as a control. Additionally, for each test, a container is prepared with soil covering the seeds having no butachlor herbicide. Only the measured amount of safening agent is incorporated into the soil covering the seeds to ascertain any herbicidal effect of the safening agent alone. For each test, the herbicidal effect of the butachlor herbicide is observed from a container treated with the same quantity of herbicide alone.

The "safening effect" is determined by adding the herbicidal effect of the butachlor herbicide when applied alone (A) to the herbicidal effect of the safening agent when applied alone (B) (in no instance, however, will this sum be taken as greater than 100), subtracting from that sum the herbicidal effect obtained when both the herbicide and safening agent are incorporated into the soil (C) as discussed above to obtain a difference (D), and then calculating the percent reduction of herbicidal effect by dividing said difference by said sum. This is graphically shown below.

$$(A + B) - C = D$$
$$100 \times \frac{D}{A + B} = \text{Safening Effect (\%)}$$

The test results which follow will serve to exemplify the reduction in the inhibition of rice plants which is achieved when butachlor herbicide is used in conjunction with a safening agent of this invention. Said agents are identified by the numbers which they were given in the list of representative compounds, above. The rate of application shown is in kilograms per hectare.

It will be understood that the safening agents in the table below were not all tested at the same time, but that control containers were employed at each test initiation. Where two or more safening agents did have the same test initiation date, the safening agent numbers are bracketed in the table.

| Phenacylidene Phthalide | Rate | Butachlor Rate | Safening Effect |
|---|---|---|---|
| 1 | 4.48 | 4.48 | 40% |
| [ 2 | 4.48 | 4.48 | 84% |
|   3 ] | 4.48 | 4.48 | 45% |
| [ 5 | 8.96 | 4.48 | 69% |
|   6 ] | 8.96 | 4.48 | 79% |
| 7 | 8.96 | 4.48 | 60% |
| 8 | 8.96 | 4.48 | 39% |
| [ 9 | 8.96 | 4.48 | 27% |
|   11 ] | 8.96 | 4.48 | 64% |
| 12 | 8.96 | 4.48 | 20% |
| 13 | 8.96 | 4.48 | 30% |
| 14 | 8.96 | 4.48 | 35% |
| 15 | 8.96 | 4.48 | 76% |
| [ 16 | 8.96 | 4.48 | 63% |
|   17 | 8.96 | 4.48 | 31% |
|   18 ] | 8.96 | 4.48 | 19% |
| 19 | 8.96 | 6.72 | 33% |

It should be pointed out the above test procedures were also carried out with a number of related isomers, homologs and analogs of the 3-phenacylidene phthalides of the invention. Such related compounds either failed to demonstrate any safening effect or produced an effect which was not deemed to be of significant magnitude.

The herbicide, safening agent or mixture thereof may be applied to the plant or plant growth medium alone, or the hebicide, safening agent or mixture thereof may be applied in conjunction with a material referred to in the art as an adjuvant in liquid or solid form. Mixtures containing the herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant or plant growth medium, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention can be accomplished by incorporating the compositions in the soil or other media.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A method of reducing injury to upland rice due to the application thereto of butachlor herbicide which comprises applying to said rice or to the growth medium an effective safening amount of a compound of the formula

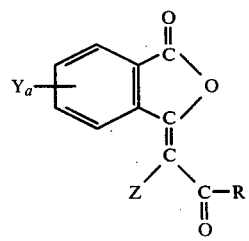

wherein R is selected from phenyl,

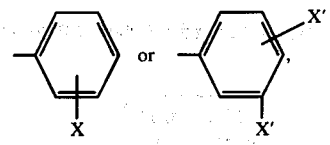

X is selected from methyl, trifluoromethyl, bromo, fluoro, 2'-chloro, 2'-nitro, 4'-phenyl and 2' or 3'-methoxy, X' is methoxy or ethoxy, Y is selected from 4-methoxy and 4 or 5-chloro, Z is hydrogen or bromo, and a is zero or one.

2. A method as defined in claim 1 wherein Z is hydrogen.

3. A method as defined in claim 2 wherein R is

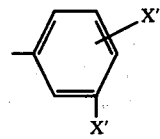

4. A method as defined in claim 3 wherein R is 2',5'-dimethoxyphenyl.

5. A method as defined in claim 4 wherein a is zero.

6. A method as defined in claim 2 wherein a is zero and R is 2' or 3'-methoxyphenyl.

7. A method as defined in claim 6 wherein R is 2'-methoxyphenyl.

8. A method as defined in claim 6 wherein R is 3'-methoxyphenyl.

9. A method as defined in claim 1 wherein the weight ratio of butachlor herbicide to said compound is from 1:5 to 5:1.

10. A method of reducing herbicidal injury to upland rice which comprises applying to said rice or to the growth medium an effective amount of a mixture comprising a herbicidally effective amount of butachlor herbicide and an effective safening amount of a compound of the formula

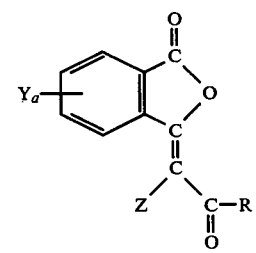

wherein R is selected from phenyl,

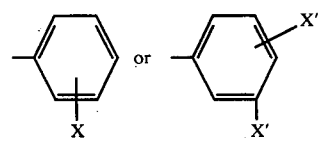

X is selected from methyl, trifluoromethyl, bromo, fluoro, 2'-chloro, 2'-nitro, 4'-phenyl and 2' or 3'-methoxy, X' is methoxy or ethoxy, Y is selected from 4-methoxy and 4 or 5-chloro, Z is hydrogen or bromo, and a is zero or one.

11. A method as defined in claim 10 wherein Z is hydrogen.

12. A method as defined in claim 11 wherein R is

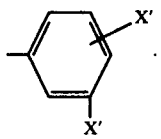

13. A method as defined in claim 12 wherein R is 2',5'-dimethoxyphenyl.

14. A method as defined in claim 13 wherein a is zero.

15. A method as defined in claim 11 wherein a is zero and R is 2' or 3'-methoxyphenyl.

16. A method as defined in claim 15 wherein R is 2'-methoxyphenyl.

17. A method as defined in claim 15 wherein R is 3'-methoxyphenyl.

18. A method as defined in claim 10 wherein the weight ratio of butachlor herbicide to said compound is from 1:5 to 5:1.

19. A mixture which comprises a herbicidally effective amount of butachlor herbicide and an effective safening amount of a compound of the formula

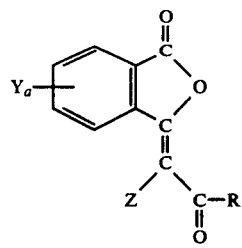

wherein R is selected from phenyl,

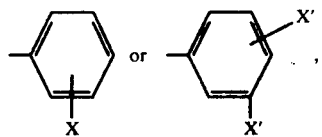

X is selected from methyl, trifluoromethyl, bromo, fluoro, 2'-chloro, 2'-nitro, 4'-phenyl and 2' or 3'-methoxy, X' is methoxy or ethoxy, Y is selected from 4-methoxy and 4 or 5-chloro, Z is hydrogen or bromo, and a is zero or one.

20. A mixture as defined in claim 19 wherein Z is hydrogen.

21. A mixture as defined in claim 20 wherein R is

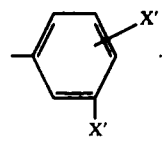

22. A mixture as defined in claim 21 wherein R is 2',5'-dimethoxyphenyl.

23. A mixture as defined in claim 22 wherein a is zero.

24. A mixture as defined in claim 20 wherein a is zero and R is 2' or 3'-methoxyphenyl.

25. A mixture as defined in claim 24 wherein R is 2'-methoxyphenyl.

26. A mixture as defined in claim 24 wherein R is 3'-methoxyphenyl.

27. A mixture as defined in claim 19 wherein the weight ratio of butachlor herbicide to said compound is from 1:5 to 5:1.

* * * * *